(12) United States Patent
Shen et al.

(10) Patent No.: US 6,624,434 B1
(45) Date of Patent: Sep. 23, 2003

(54) APPARATUS FOR MEASUREMENT OF PARTICLE OR DROPLET VELOCITY

(75) Inventors: Zilan Shen, West Windsor, NJ (US); Hyoun Park, Surry (CA); Keith Graydon, Cranbury, NJ (US)

(73) Assignee: Sarnoff Corporation, Princeton, NJ (US)

( * ) Notice: Subject to any disclaimer, the term of this patent is extended or adjusted under 35 U.S.C. 154(b) by 0 days.

(21) Appl. No.: 09/553,211

(22) Filed: Apr. 20, 2000

Related U.S. Application Data

(60) Provisional application No. 60/130,324, filed on Apr. 21, 1999.

(51) Int. Cl.[7] .............................................. G01N 15/06
(52) U.S. Cl. .................. 250/573; 250/222.2; 250/208.1
(58) Field of Search ......................... 369/112; 250/573, 250/222.2, 203.1; 73/53.01, 86.1, 53.09, 1.16; 347/19; 356/338; 359/640

(56) References Cited

U.S. PATENT DOCUMENTS

| | | | | |
|---|---|---|---|---|
| 4,997,272 A | * | 3/1991 | Dopheide et al. ........... 356/28.5 |
| 5,025,438 A | * | 6/1991 | Emoto ......................... 369/112 |
| 5,074,658 A | * | 12/1991 | Tavlarides et al. ............ 356/27 |
| 5,186,057 A | * | 2/1993 | Everhart .................. 73/861.41 |
| 5,339,196 A | | 8/1994 | Grebe ......................... 359/640 |
| 5,430,306 A | | 7/1995 | Ix ............................... 250/573 |
| 5,691,483 A | * | 11/1997 | Linnemann .............. 73/861.05 |
| 6,016,194 A | * | 1/2000 | Girvin et al. ............... 356/337 |
| 6,153,873 A | * | 11/2000 | Wolf ....................... 250/208.1 |

* cited by examiner

Primary Examiner—David V. Bruce
Assistant Examiner—Hoon Song
(74) Attorney, Agent, or Firm—William J. Burke

(57) ABSTRACT

An apparatus for measuring the velocity of a droplet of a liquid includes a laser to generating a beam of light and projecting the beam along a first path. A lens is along the first path for forming the beam into the shape of a thin sheet. A beam divider is along the first path for dividing the beam into two separate beams which extend along second and third paths. The second and third paths lie in a common plane. Along the second and third paths is means for projecting a droplet of liquid across the second and third paths so that the droplet passes through both of the divided beams. AT least one photodetector is along the second and third paths to receive the divided beams and provide an electrical signal corresponding to the beams. A beam divider which can be used to divide the beam into two beams includes a body of an optically transparent material having at least two flat front surfaces which are at an angle with respect to each other to form a V having a sharp corner, and at least two flat back surfaces each of which is spaced from and parallel to a separate front surface.

13 Claims, 3 Drawing Sheets

APPARATUS FOR MEASUREMENT OF PARTICLE OR DROPLET VELOCITY

This application claims the benefit of U.S. Provisional Application Serial No. 60/130,324, filed Apr. 21, 1999.

FIELD OF THE INVENTION

The present invention is directed to an apparatus for the measurement of the shape profile and velocity of an individual particle or an individual droplet of a liquid, and also to a beam divider for use in such an apparatus.

BACKGROUND OF THE INVENTION

There has been developed an apparatus for measuring various characteristics of a droplet of a liquid, such as a droplet of ink for an ink printer. This apparatus is described in detail in the application for U.S. Letters Patent of Tzong-Shyng Leu, Ser. No. 09/215,018, filed Dec. 17, 1998. In general, this apparatus comprises a laser for generating and projecting a beam of light along a path. Along the path of the beam of light is a lens or a lens combined with a set of knife edges which forms the beam into the shape of a thin sheet at a focal point beyond the lens. Also along the path of the beam is a photodetector for receiving the beam and providing an electrical signal corresponding to the light received. Adjacent the path of the beam is means for projecting a droplet of a liquid through the sheet of the beam. The droplet passing through the beam of light varies the amount of light receiving by the photodetector which generates a corresponding signal. From the signal various characteristics of the droplet, such as size and shape, can be determined. However, for various purposes, it would be desirable to be able to measure the velocity of the droplet.

SUMMARY OF THE INVENTION

One aspect of the present invention is an apparatus for measuring the velocity of a droplet of a liquid. The apparatus includes means for generating and projecting a beam of light along a first path. Along the first beam path is means for dividing the beam into two separate beams extending along separate second and third paths. Means is adjacent the two beams for projecting a droplet of a liquid through both of the beams. Means is also provided to detect the two beams after the droplet has passed therethrough to provide electrical signals from which the velocity of the droplet can be determined.

Another aspect of the present invention is a beam divider which can be used in the apparatus for measuring the velocity of a droplet. The beam divider includes a body of a light transparent material having two light receiving surfaces. The light receiving surfaces are at an angle with respect to each other and extend from a common point to form a V. The body also includes two light emitting surfaces. Each of the light emitting surfaces is spaced from and parallel to a separate light receiving surface.

BRIEF DESCRIPTION OF THE INVENTION

DETAILED DESCRIPTION OF THE INVENTION

Figure 1:
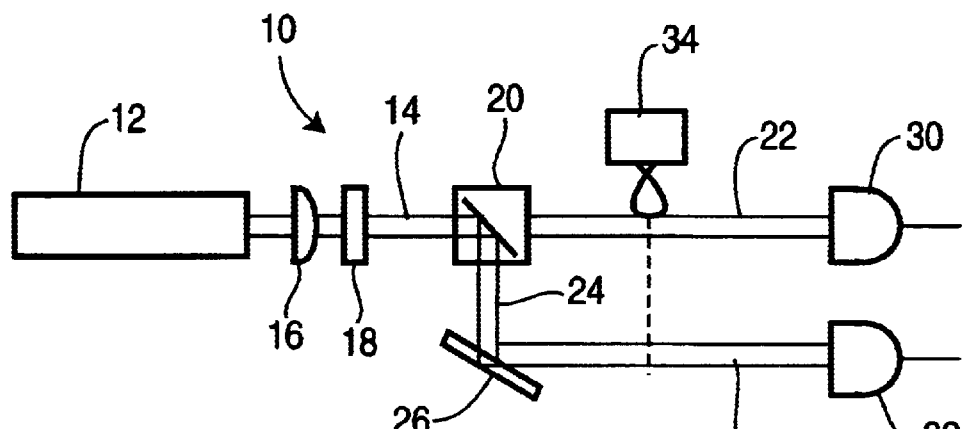
FIG. 1 is a schematic drawing of a form of the apparatus of the present invention.

Referring initially to FIG. 1, a form of the apparatus of the present invention for measuring the velocity of a drop of liquid is generally designated as 10. Measuring apparatus 10 comprises a laser 12, which os adapted to generate a beam of light and direct the beam along a path 14. Along the path 14 and in front of the laser 12 are a series of lenses and knife edges 16 and 18, which shape the beam into the form of a thin sheet. The beam the passes through a beam splitter 20, which divides the beam into two portions: one which extends along the path 22 and the other which extends along a path 24 that is substantially normal to the path 22. A mirror 26 is along the path 24 and changes the direction of the portion of the bean extending along path 24 so that the beam proceeds along a path 28 parallel to path 22. The paths 22 and 28 lie in the same plane. Separate photodetectors 30 and 32 are along the paths 22 and 28 and are adapted to receive the beams extending along paths 22 and 28, respectively. The photodetectors 30 and 32 are adapted to provide an electrical signal corresponding to the beam received thereby. Adjacent the path 22 is a device 34 for generating and projecting a droplet of a liquid, such as the print head of an ink jet printer. The device 34 is positioned so as to project a droplet of a liquid toward and through the beam extending along the path 22.

Figure 4:
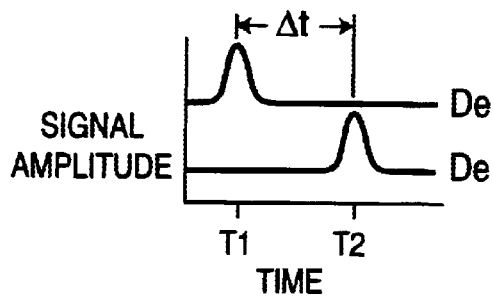
FIG. 4 is a graph showing the electrical signals produced by the apparatus of FIG. 2.
Figure 5:
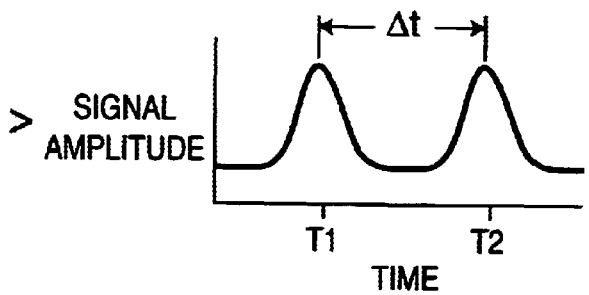
FIG. 5 is a graph showing the electrical signals produced by a variation of the apparatus shown in FIG. 2.

In the operation of the apparatus 10, after the droplet of liquid passes through the portion of the beam extending along the path 22, it will pass through the portion of the beam extending along the path 28 since the portion of the beam extending along the path 28 is parallel to the portion of the beam extending along the path 22. Since the two paths 22 and 28 are spaced apart, the droplet of liquid will pass through the portion of the beam extending along the path 28 at a later time then when its passes through the portion of the beam extending along the path 22. As the droplet of liquid passes through each of the portions of the beam, it disrupts the beam so as to change the amount of light received by each of the photodetectors 30 and 32. This results in a change in the electrical signal provided by each of the photodetectors 30 and 32. Referring to FIG. 4, it can be seen that the first photodetector 30 provides a change in its output signal first at time T1, whereas the second photodetector 30 provides a change in its output signal as a later time T2. By determining the difference between times T1 and T2, and knowing the distance between the two parallel paths 22 and 28, the velocity of the droplet of the liquid can be determined. Thus, the apparatus 10 can be used to measure the velocity of a droplet of liquid, as well as the profile of the liquid. The apparatus 10 can also be used to measure the velocity of any particle which can be projected through the beams of light and will disrupt the amount of light which is received by the photodetectors 30 and 32.

Figure 2:
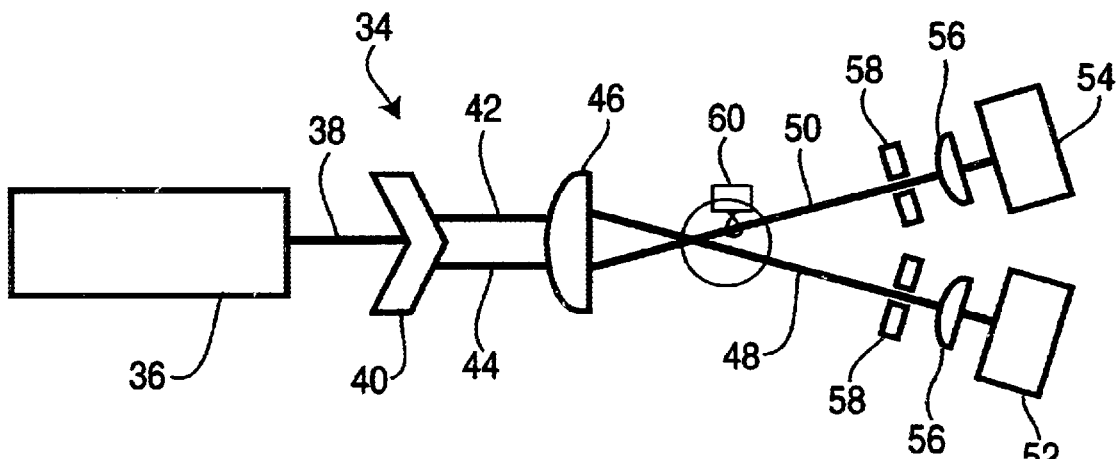
FIG. 2 is a schematic drawing of a preferred form of an apparatus of the present invention.

Referring to FIG. 2, a preferred form of the velocity measurement apparatus of the present invention is generally designated as 34. Apparatus 34 comprises a laser 36 which is adapted to generate and project a beam of light along a path 38. Although not shown, the laser 34 has in front of it, lenses of lenses combined with knife edges which shape the beam of light into the form of a thin sheet. Along the beam path 38 is a beam divider 40, the details of which will be described later. However, the divider 40 divides the beam into two separate beams which are emitted from the divider 40 along two separate, spaced and parallel paths 42 and 44. Along the beam paths 42 and 44 is a focusing lens system 46 which receives the beams and deflects both of the beams so that the beams then travel along paths 48 and 50 which cross each other beyond the lens 46. The beam paths 48 and 50 lie in the same plane. Along each of the beam paths 48 and 50 is a separate photodetector 52 and 54 respectively. The photodetectors 52 and 54 are adapted to receive the beams which extend along the beam paths 46 and 48 and provide an electrical signal output corresponding to the light received. In front of each of the photodetectors 50 and 52 and along their respective beam paths 46 and 4 is a collecting lens 56 and a mask 58. The masks 58 and collecting lenses 56 serves to confine the respective beams and direct the into the photodetectors.

Figure 3:
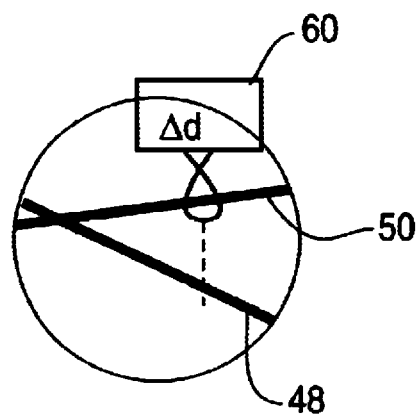
FIG. 3 is an enlarged showing of the circled portion of FIG. 2.

As shown more clearly in FIG. 3, at a point along the beam path 50 beyond the point where the beam paths 48 and 50 cross each other is a device 60 for generating a droplet of a liquid and projecting the droplet toward and through the beam extending along the beam path 50. The droplet forming device 60 may be the head of an ink jet printer. In the operation of the apparatus 34, the droplet of liquid passes first through the beam which extends along the beam path 50 and then continues to pass through the beam which extends along the beam path 48. As the droplet passes through each beam, it disrupts part of the beam and thereby changes the output signal from each of the photodetectors 52 and 54. Since the points along the beam paths 48 and 50 at which the droplet passes through the beams are spaced from each other, the change in the electrical output signal from the photodetectors 52 and 54 will be at different times. Referring to FIG. 4, it can be seen that the change in the electrical signal from the photodetector 52 will be at a time T1 and the change in the electrical signal from the photodetector 54 will be at a later time T2. By measuring the distance between the beam paths 48 and 50 at the points where the droplet of liquid passes through the beams, and by determining the time difference between the change in electrical output signals of the photodetectors, 52 and 54, the velocity the droplet can be determined. The spacing between the beam paths 48 and 50 where the droplet passes thereacross can be varied by moving the droplet forming device 60 along the beam paths 48 and 50, or by varying the structure of the focusing lens system 46, or as will be described, by varying the structure of the beam divider 40.

Figure 6:
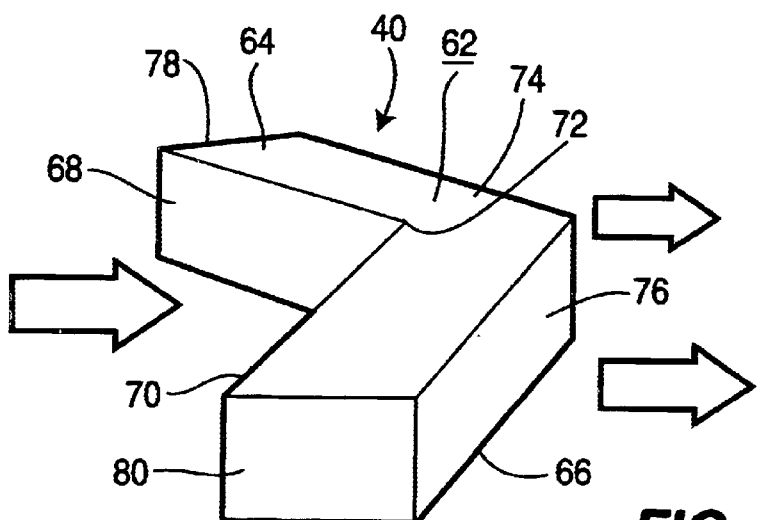
FIG. 6 is a perspective view of the beam divider of the apparatus shown in FIG. 2.

Referring to FIG. 6, there is shown a perspective view of the beam divider 40. Beam divider 40 comprises a body 62 of an optically transparent material, such as glass. The body 62 has spaced, opposed, substantially flat surfaces 64 and 66. At the front or light receiving side of the body 62 are two substantially flat surfaces 68 and 70, which extend between the top and bottom surfaces 64 and 66. The front surfaces 68 and 70 are arranged at an angle with respect to each other and extend forwardly of the body 62 from a common line 72. Thus, the front surfaces 68 and 70 form a V. A pair of substantially flat back or light emitting surfaces 74 and 76 extend between the top and bottom surfaces 64 and 66. The back surface 74 is spaced from and parallel to the front surface 68, and the back surface 76 is spaced from and parallel to the front surface 70. The body 62 also has an end surface 78 extending between the ends of the front and back surfaces 68 and 74, and an end surface 80 extending between the end of the front and back surfaces 74 and 76.

Figure 7:
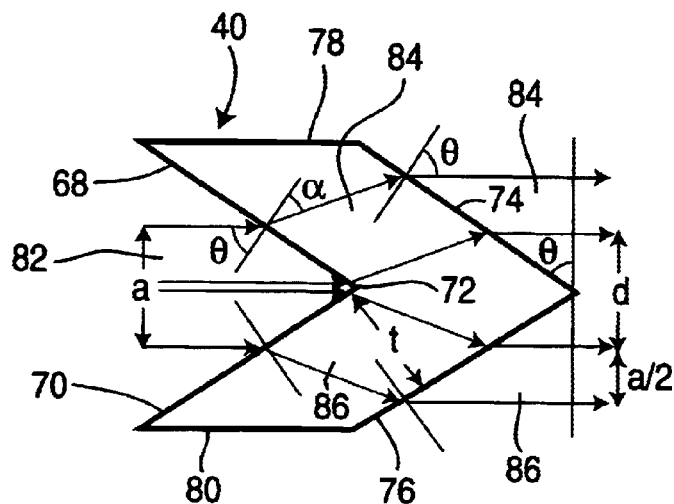
FIG. 7 is a top view of the beam divider shown in FIG. 6 showing the manner in which the beam divider operates.

Referring to FIG. 7, there is shown the manner that the beam divider 40 operates. A beam 82 having a width a is directed into the body 62 at the front surfaces 68 and 70. The width of the beam 82 is such that the beam 82 can be directed into the body 62 with a portion of the beam 82 entering the body 62 along a portion of the front surface 68, and the other portion of the beam 82 enters the body 62 along a portion of the font surface 70. The beam portions 84 and 86 which enter body 62 through the front surfaces 68 and 70 respectively, are deflected by their respective front surfaces 68 and 70 so that they are directed away from each other. The beam portions 84 and 86 flow through the body 62 to the back surfaces 74 and 76 respectively. When the beam portions 84 and 86 pass through their respective back surfaces 74 and 76 they are deflected so as to be directed along paths parallel to the path of the original beam 82. Thus, the beam divider 40 divides the single beam 82 into two separate beams 84 and 86 which are directed along spaced, parallel paths. The thickness of the body 62 between the front surfaces 68 and 70 and the back surfaces 74 and 76 along with the incident angles of the front surfaces 68 and 70 determine the spacing between the emitted beams 84 and 86. By increasing the thickness of the body 62 and increasing the incident angles, the spacing between the emitted beams 84 and 86 can be increased. Although the beam divider 40 os shown as having two front and back surfaces so as to divide a beam into two separate beams, by providing the body 62 with more than two front surfaces and back surfaces, the beam divider 40 can provide more than two sub-beams.

Figure 8:
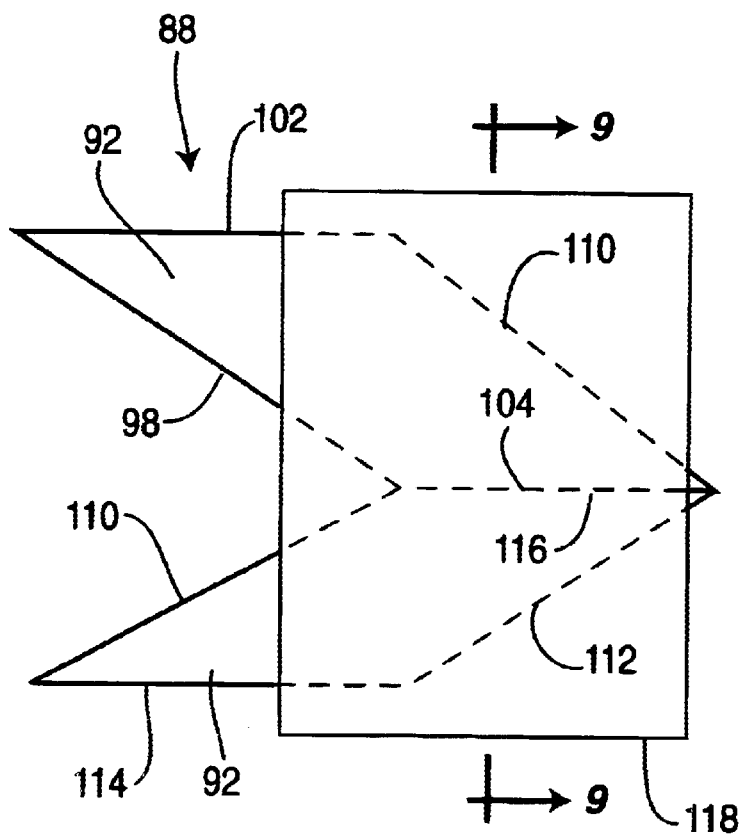
FIG. 8 is a top view of a modification of the beam divider of FIG. 6.
Figure 9:
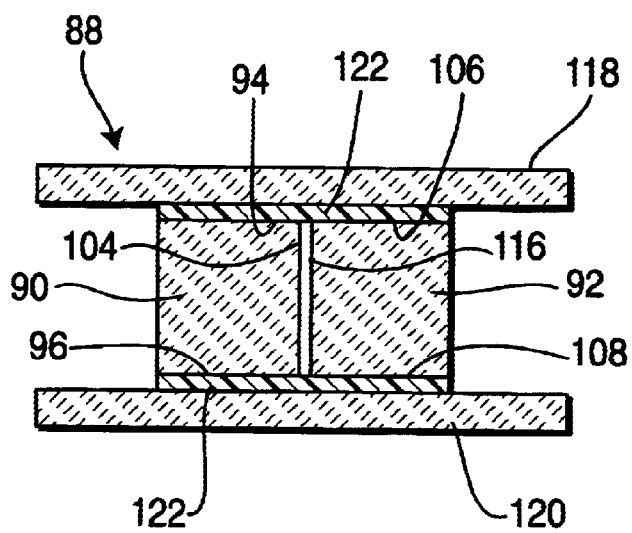
FIG. 9 is a sectional view along line 9—9 of FIG. 8.

In the beam divider 40, the optical quality of the incident surfaces is very important to achieve the proper division of the beam. This is especially so at the line 72 where the front surfaces 68 and 70 meet and where the incident beam is separated. The surfaces at this line must be flat and clean, and the corner has to be sharp. However, sharp angles are difficult to produce. Referring to FIGS. 8 and 9 there is shown a shown another form of the beam divider of the present invention, generally designated as 88, which can be more easily made with the desired flatness and sharpness. In the beam divider 88, the body is formed of two separate pieces 90 and 92, each of which forms one-half of the body. The body piece 90 has flat top and bottom surfaces 94 and 96, flat front and back surfaces 98 and 100, an outer end surface 102 and an inner end surface 104. The top and bottom surfaces 94 and 96, front and back surfaces 98 and 100 and outer end surface 102 are identical to the corresponding surfaces of one-half of the body 62 of the beam divider 40. The body piece 92 has flat top and bottom surfaces 106 and 108, flat front and back surfaces 110 and 112, an outer end surface 114 and an inner end surface 116. The top and bottom surfaces 106 and 108, front and back surfaces 110 and 112 and outer end surface 114, are identical to the corresponding surfaces of the other half of the body 62 of the beam divider 40. The inner end surfaces 104 and 116 of the body potions 84 and 86 are at an angle with respect to the front and back surfaces such that when the two body portions 84 and 86 are placed together with the inner end surfaces 104 and 116 contacting each other, the front surfaces 98 and 110 of the body portions 84 and 86 are the desired angle. Likewise the back surfaces 100 and 112 are at the desired angle with respect to each other. A top plate 118 is placed of the aligned top surfaces 94 and 106 of the body pieces 90 and 92, and a bottom plate 120 is placed on he aligned bottom surfaces 96 and 108 of the body pieces 90 and 92. The top and bottom plates 118 and 120 are secured to the body pieces 90 and 92 with a suitable cement 112 between the top and bottom plates 118 and 120 and the top surfaces 94 and 106 and the bottom surface 96 and 108 of the body pieces 90 and 92. Thus, the two body pieces 90 and 92 are firmly secured together with the front surfaces 98 and 110 being at the proper angle with respect to each other.

By forming the body of two separate pieces, all of surfaces of the two body pieces can be easily formed flat and at the proper angle by suitable grinding. Thus, when the body pieces are secured together, the front surfaces will be at the proper angle with respect to each other and the junction of the front surfaces will form a sharp corner. Since the body pieces are secured together only by cement between the top and bottom plates and the top and bottom surfaces of the body pieces, there is no cement between the inner end surfaces of the body pieces which interferes with the sharpness of the corner between the front surfaces. If desired, a groove may be formed in the inner surface of one of the top and bottom plates in which the body pieces fit. This will hold the body pieces in place which the parts are cemented together.

Thus, there is provided by the present invention an apparatus for measuring the velocity of a droplet of a liquid or a particle. The apparatus includes a laser for generating a beam of light and projecting the beam along a path. The beam os formed into the shape of a thin sheet. The beam is then divided into two separate beams which are guided along separate and parallel paths to a photodetector which generates and electrical signal based on the intensity of the beam received. The beams may be directed into separate photodetectors or into a single photodetector. Means is provided along the path of one of the beams for generating the droplet of the liquid and projecting the droplet through the beams in succession. When the droplet passes through each of the beams it disrupts the beam so as to vary the signal provided by the photodetector receiving the beam. Thus, the photodetector of photodetectors provide two separate signals as different times. By measuring the time interval between the two signals and the distance between the two parallel beams, the velocity of the droplet can be determined. The present invention also provides a beam divider which will divide a beam into two of more portions and eject the beams along separate and parallel paths.

What is claimed is:

1. An apparatus for measuring the velocity and profile of a droplet of liquid comprising:
   a light source for generating a beam of light and directing the beam along a first path;
   a beamsplitter along said first path for dividing the beam into two separate beams which extend along second and third paths;
   a lens along the second and third paths for diverting the beams extending along the second and third paths such that the beams cross each other, and
   a plurality of photodetectors for detecting the two beams after a droplet of liquid passes therethrough at two different times and for providing an electrical signal corresponding to the beams.

2. The apparatus of claim 1 wherein the beamsplitter projects the two beams along second and third paths which lie in the same plane so that the droplet of liquid can be projected along a single path through both of the divided beams.

3. The apparatus of claim 2 including at least one photodetector along the second and third paths for receiving the beams and providing electrical signals corresponding to the beams.

4. The apparatus of claim 3 including two photodetectors with one of the photodetector being along the second path and the other photodetector being along the third path.

5. The apparatus of claim 4 in which the light source is a laser.

6. The apparatus of claim 5 including at least one additional lens and at least one knife edge along the first path between the laser and the beam divider for forming the beam into the shape of a thin sheet.

7. The apparatus of claim 2 wherein the beamsplitter is a beam divider which projects the two beams along second and third paths which are parallel to each other between the beam divider and the lens.

8. The apparatus of claim 7 wherein the droplet of liquid passes through the beam paths at a point after the second and third paths cross each other.

9. The apparatus of claim 8 including at least one photodetector along the second and third paths for receiving the beams and providing electrical signals corresponding to the beams.

10. The apparatus of claim 9 including two photodetectors with one of the photodetectors being along the second path and the other photodetector being along the third path.

11. The apparatus of claim 10 in which the light source is a laser.

12. The apparatus of claim 11 including at least one additional lens and at least one knife edge along the first path between the laser and the beam divider for forming the beam into the shape of a thin sheet.

13. The apparatus of claim 7 in which the beam divider comprises a body of an optically transparent material having at least two flat front surfaces which are at an angle with respect to each other to form a $V_1$ and at least two back surfaces each of which is spaced from and parallel to a separate first surface, the first surfaces are positioned to face the light source so as to receive the light beam and divide the beam into at least two beams which flow through the body to the back surfaces, and the back surfaces project the separate beams therefrom along parallel paths.

* * * * *

UNITED STATES PATENT AND TRADEMARK OFFICE
CERTIFICATE OF CORRECTION

PATENT NO. : 6,624,434 B1
DATED : September 23, 2003
INVENTOR(S) : Shen et al.

It is certified that error appears in the above-identified patent and that said Letters Patent is hereby corrected as shown below:

Column 2,
Line 17, please change "os" to -- is --.
Line 26, please change "bean" to -- beam --.
Line 54, please change "30" to -- 32 --.

Column 3,
Line 19, please change "46 and 4" to -- 46 and 48 --.
Line 22, please change "the into" to -- them into --.

Column 4,
Line 29, please change "os" to -- is --.

Column 5,
Line 3, please change "112" to -- 122 --.
Line 28, please change "os" to -- is --.

Column 6,
Line 49, please change "$V_1$" to -- V, --.

Signed and Sealed this

Thirteenth Day of January, 2004

JON W. DUDAS
*Acting Director of the United States Patent and Trademark Office*